United States Patent
Hessel et al.

(10) Patent No.: US 6,709,422 B2
(45) Date of Patent: Mar. 23, 2004

(54) OSTOMY BAG WITH COUPLING

(75) Inventors: Lasse L Hessel, Svendborg (DK); Jesper Malling, Svendborg (DK)

(73) Assignee: Biotap A/S, Svendborg (DK)

( * ) Notice: Subject to any disclaimer, the term of this patent is extended or adjusted under 35 U.S.C. 154(b) by 0 days.

(21) Appl. No.: 10/187,765

(22) Filed: Jul. 1, 2002

(65) Prior Publication Data

US 2002/0165507 A1 Nov. 7, 2002

Related U.S. Application Data

(63) Continuation of application No. PCT/DK01/00008, filed on Jan. 5, 2001.

(30) Foreign Application Priority Data

Jan. 7, 2000 (DK) .......................................... 2000 00025

(51) Int. Cl.⁷ ................................................ A61F 5/44
(52) U.S. Cl. ..................................................... 604/342
(58) Field of Search .......................... 604/332, 338–342; 215/282, 287

(56) References Cited

U.S. PATENT DOCUMENTS

| 3,805,337 | A | * | 4/1974 | Branstetter | ..................... | 24/27 |
| 3,964,485 | A |   | 6/1976 | Neumeier | ................... | 128/283 |
| 5,026,360 | A |   | 6/1991 | Johnsen et al. | ............. | 604/338 |
| 5,322,523 | A | * | 6/1994 | Olsen | ........................ | 604/338 |
| 5,496,297 | A | * | 3/1996 | Olsen | ........................ | 604/339 |
| 5,647,861 | A |   | 7/1997 | Steer et al. | .................. | 604/342 |
| 5,662,629 | A |   | 9/1997 | Steer et al. | .................. | 604/342 |
| 5,830,200 | A |   | 11/1998 | Steer et al. | .................. | 604/338 |
| 5,843,053 | A | * | 12/1998 | Steer | ........................... | 604/342 |
| 5,902,295 | A | * | 5/1999 | Steer et al. | .................. | 604/339 |
| 5,957,905 | A | * | 9/1999 | Steer | ........................... | 604/338 |
| 6,409,710 | B1 | * | 6/2002 | Holtermann | ................. | 604/342 |
| 2001/0004687 | A1 | * | 6/2001 | Plass et al. | ................. | 604/338 |
| 2002/0032417 | A1 | * | 3/2002 | Holtermann | ................. | 604/338 |

FOREIGN PATENT DOCUMENTS

GB    1598309    9/1981

* cited by examiner

Primary Examiner—Weilun Lo
Assistant Examiner—Michael G. Bogart
(74) Attorney, Agent, or Firm—Winston & Strawn LLP

(57) ABSTRACT

An ostomy bag with a wall of a flexible material and a first coupling member for detachably coupling the ostomy bag with an implant, for example an implant surrounding the stoma, with the first coupling member being and designed with a circumferential groove. The first coupling member is a spring ring composed of a spring wire having end parts extending a distance past each other. Along the opening of the ostomy bag, an edge reinforcement is made by joining of at least a part of the spring ring and an area of the wall of the ostomy bag, and on each end part of the spring wire is a handle for opening the spring ring on overcoming the spring power in the spring ring so that the edge reinforcement can pass over the circumferential groove of the implant at mounting and decoupling of the ostomy bag.

11 Claims, 3 Drawing Sheets

OSTOMY BAG WITH COUPLING

CROSS-REFERENCE TO RELATED APPLICATIONS

This application is the U.S. national stage designation of International application PCT/DK01/00008 filed Jan. 5, 2001, the content of which is expressly incorporated herein by reference thereto.

BACKGROUND ART

The invention relates to an ostomy bag of the kind that comprises a flexible wall having an opening for receiving a stoma, and a coupling for coupling the ostomy bag with a mainly annular implant fitted around the stoma. The implant has a circumferential groove along its outer part, and the coupling has the form of a spring ring with overlapping end parts shaped as handles arranged to open the spring ring when they are pressed together manually.

It is generally known to adhere ostomy bags to the skin around a stoma, e.g., a colostomy. Known ostomy bags can either adhere directly to the skin or, if desired, can be adhered to an adhesive disc provided with attachment means for the ostomy bag. The attachment means can have different designs.

U.S. Pat. No. 4,917,691 discloses ostomy equipment comprising an ostomy bag having a first coupling member and a second coupling member that is part of a device for being adhered around the stoma. The first coupling member has a collar with a lip for snap engagement with a deformable collar in the second coupling member. The coupling members are squeezed together and a ring with a ratchet lock serves for drawing the coupling members tightly together.

Ostomy bags with coupling devices based on similar principles are known from U.S. Pat. Nos. 5,269,773 and 4,685,990.

European patent application 853933 discloses another type of coupling that also comprises, respectively, a first coupling member on an ostomy bag and a second coupling member that is part of a device that is adhered around the stoma. These coupling members engage with each other through the action of an inserted locking ring. The locking ring has two handles that initially are pressing in a direction away from each other in order to reduce the diameter of the ring so that it can be put under catches on the adhesive coupling member. During mounting of the coupling member of the ostomy bag on the adhered coupling member, the diameter of the ring is forced to increase in order to, after mounting, spring back to form sealing between the surfaces of the coupling members. Such a locking ring cannot be used for mounting of its associated ostomy bag on an annular implant that completely lacks a correspondingly arranged second coupling member.

What these known ring coupling systems have in common is that they are composed of a coupling member adhered to the skin around the stoma, and a coupling member extending from the opening in the ostomy bag which is to receive the stoma. These coupling systems are therefore bulky and awkward for a patient to use, and a reliable fastening of a coupling member depends on prior careful cleaning of the skin to reduce the risk of leakage.

A considerable part of these disadvantages is remedied by the inventions according to the inventor's prior U.S. patent applications, including Ser. No. 09/103,919 and DK/PA 1999 01026, each of which is expressly incorporated herein by reference thereto. From these, implants are known for implantation in an animal or human body and comprising an inner part for fastening in the body, and an outer part extending outward from the body and serving for mounting of e.g., an ostomy bag, which can be detachably connected with the body via the implant.

The coupling means of ostomy bags mentioned above and applied so far can in a few cases be applied to couple the ostomy bag onto the implant but these coupling means are not directly designed for this purpose. The ostomy bag can therefore not always be coupled optimally onto the implant and can therefore not form a completely tight connection with it. For example, small differences in diameters of the coupling means cause a very loose coupling that cannot effectively ensure against leakage.

To couple the ostomy bag with the implant or to decouple the ostomy bag, it can furthermore be necessary to either twist and press the ostomy bag toward the implant or to pull at the ostomy bag, but these motions can cause malaise and inconveniences in form of pains or bleedings in the places where the implant is in contact with tissue.

Locking rings designed to ensure that the coupling means are pressed tightly together are often difficult to manipulate, and a locking ring can, in the cases where the locking mechanism of the lock ring cannot be released, have the very unfortunate consequence that the ostomy bag to be changed has to clipped or cut off the implant.

The present invention now overcomes the shortcomings of the prior art.

SUMMARY OF THE INVENTION

The present invention provides an ostomy bag of the kind mentioned in the opening paragraph. In a simple manner and without causing inconvenience to the patient who has had an implant implanted around a stoma, this ostomy bag can both be coupled onto an implant of the above kind to form a tight-fitting connection between the implant and the ostomy bag, and can be quickly and easily decoupled the implant in a similarly simple manner when the ostomy bag is to be changed.

The novel and unique features according to the invention, whereby this is achieved, is the fact that the spring ring is composed of a spring wire having, in a position of rest, a diameter that is smaller than the smallest diameter of the circumferential groove of the implant. It also has an edge reinforcement made along the opening of the ostomy bag which is formed by joining at least a part of the spring ring and an area of the wall of the ostomy bag, such that the edge reinforcement, upon coupling of the ostomy bag and the implant o a mounted position, serves for being received in the circumferential groove of the implant. Also, when manually pressed towards each other, the handles are provided and arranged to be able to open the spring ring at least so much that the diameter of the spring ring and edge reinforcement are each made larger than the largest diameter of the circumferential groove of the implant.

When the end parts of the spring ring overlap each other, these end parts can pass over each other slidably so that the size of the opening of the coupling easily can be changed, and easily can be taken in over a second coupling member, such as an implant.

A part of the spring ring and an area of the wall of the ostomy bag can be joined to form an edge reinforcement along the opening of the ostomy bag. This edge reinforcement can completely or partly surround the spring wire of the spring ring so that at least part of the spring ring is integrated inside in the ostomy bag.

The edge reinforcement can advantageously be formed from at least a part of the spring ring and an area of the wall around the opening of the ostomy bag so that this wall area is wrapped at least partly around the spring wire of the spring ring. Thus, upon joining of the ostomy bag and the implant, the edge reinforcement will be received in the circumferential groove of the implant.

By allowing the area of the ostomy bag wall, which together with the spring ring form the edge reinforcement around the opening of the ostomy bag, to extend over the entire periphery of this opening, the edge reinforcement can be pressed together so that the ostomy bag expediently can be guided down over the implant without the wall of the ostomy bag being damaged.

The spring ring has two handles made on the overlapping end parts of the spring ring and arranged to, when they are pressed together manually, open the spring ring at least so much that the diameter of the spring ring and edge reinforcement are each made larger than the largest diameter of the circumferential groove of the implant. This facilitates connection of the ostomy bag to the stoma or removal of the ostomy bag from the stoma.

When each of the end parts of the spring wire has a handle, the spring power in the spring ring can easily be overcome by pressing the handles towards each other with e.g., two fingers, in order to open the spring ring so that the opening of the edge reinforcement is made sufficiently large to be able to pass over the circumferential groove of the implant at mounting and decoupling of the ostomy bag.

The spring ring can advantageously be designed to have a spring power that is so great that the edge reinforcement can be detachably clamped to abut closely against the circumferential groove of the implant when the handles are released to bring the ostomy bag into its mounted and rigidly coupled state on the implant.

At least along the area where the end parts of the spring ring are extending past each other, these end parts can be provided with opposite plane surfaces which, in the mounted state, lie adjacent or in contact with each other so that the end parts at the areas with the plane surfaces combined have the same or mainly the same diameter across the plane surfaces as the diameter of the rest of the spring wire when the end parts are touching each other so that the edge reinforcement has the same thickness in its full extent in the mounted state of the ostomy bag.

When the edge reinforcement is embedded in the circumferential groove of the implant, the spring ring can therefore be fixed in this groove so that the ostomy bag is anchored and closing tightly against the implant.

BRIEF DESCRIPTION OF THE DRAWINGS

The invention will be explained in greater detail below, describing only exemplary embodiments with reference to the drawing, in which.

DETAILED DESCRIPTION OF PREFERRED EMBODIMENTS

By this invention, a stomi-operated patient is given a so far unknown security and certainty that the ostomy bag will not come off, be dislocated or pulled off, and also the certainty that the ostomy bag will not leak where it is joined with the implant.

In an especially advantageous embodiment, the handles of the spring ring can be located inside the ostomy bag so that the handles will not get caught in the clothes. When the handles are located inside the ostomy bag, the user of the ostomy bag cannot feel them when the bag is worn.

The handles of the spring ring can either be formed by the same spring wire as the rest of the spring ring or each handle can be designed with a flexible projection extending in opposite directions and serving as abutment to a finger at opening of the spring ring.

Alternatively, each handle can be designed as an eye formed by the same spring wire as the rest of the spring ring.

When the spring ring in addition is provided with a clamp connecting the free ends of the handles, the clamp can advantageously serve for locking the spring ring in the circumferential groove of the implant.

When the ostomy bag is to be demounted, the clamp is easily pulled back to allow the handles of the spring ring to be pressed towards each other again so that the spring ring can be opened and taken off the implant.

The spring ring can be made of e.g., spring steel or a plastic material, such as e.g., polyethylene, ethylene, polypropylene, or copolymerized vinyls having similar resilient properties, so that the ostomy bag is inexpensive to manufacture and easy to use.

When it is necessary to change the ostomy bag, for example when it is full, this can be done in one simple and quick action that can be done discretely and without the usual, known preparations, such as cutting a hole in the adherent of the ostemy bag or in the adhesive disc. When replacing the bag, prior cleaning of the skin to ensure optimal adherence of the ostomy bag or the adhesive disc is not necessary.

When, e.g., a dischargeable ostomy bag is used, the same ostomy bag can be used for a significantly longer period of time than hitherto known bags without having to be replaced.

The ostomy bag according to the invention is therefore both quick, easy and hygienic to use and also economical, and the amount of foul plastic waste which has to be disposed of is less than conventionally in connection with use of ostomy bags.

Figure 1:
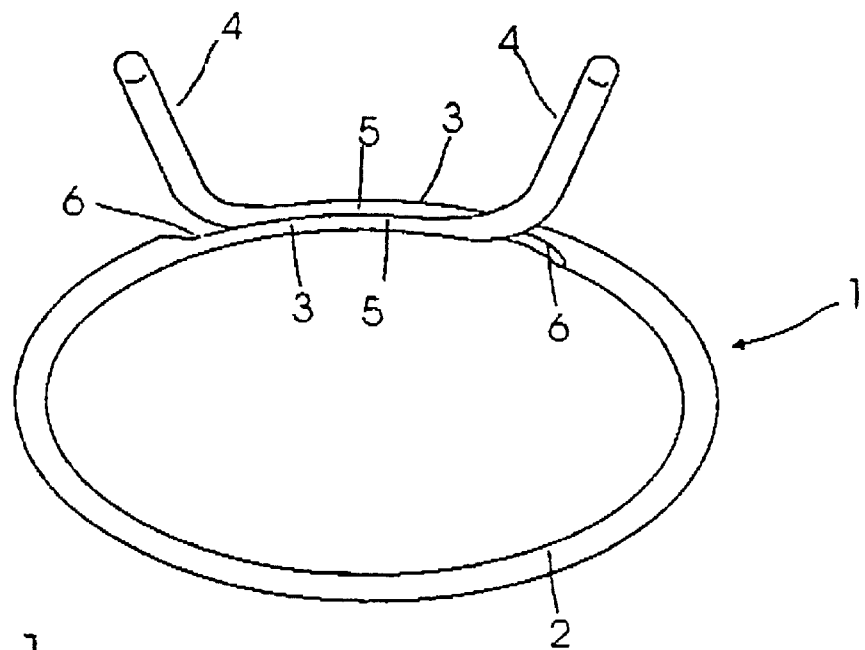
FIG. 1 is a perspective view of a first embodiment of a spring ring for an ostomy bag according to the invention.

Referring now to the drawings, FIG. 1 shows a spring ring 1 comprising a spring wire 2, end parts 3, and handles 4 which form part of the spring wire 2. The end parts 3 have an area 5 where they are extending past each other and where they have opposite plane surfaces 6. The plane surfaces 6 combined have the same diameter across the surfaces as the diameter of the rest of the spring wire 2. The handles 4 are resilient and function as abutments to the fingers when the spring ring is to be mounted or decoupled.

Alternatively, the handles 4 can be designed as eyes (not shown) made of extensions of the spring wire.

Figure 2:
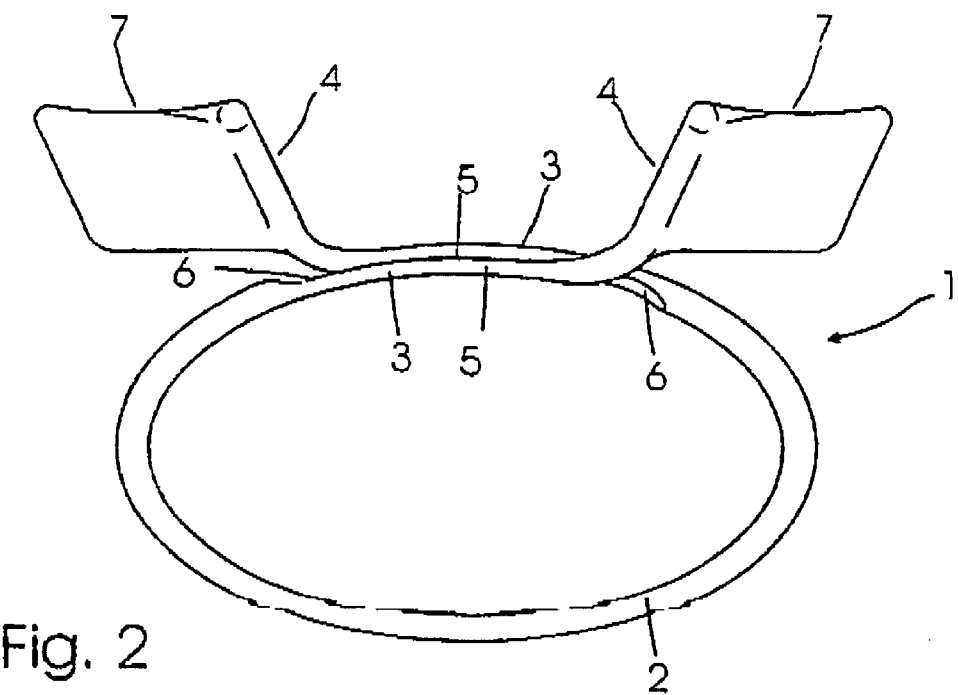
FIG. 2 is a perspective view of a second embodiment of a spring ring for an ostomy bag according to the invention.

FIG. 2 shows a second embodiment of a spring ring 1 for an ostomy bag 8 according to the invention. This embodiment corresponds to the embodiment in FIG. 1, but the handles 4 are in this case designed with projections 7 each serving as abutment to a finger. The projections are extending away from each other, and the projections can be made of a resilient material so that they are easy to lay hold of and easily return to a position mainly flush with the ring. The projections therefore do not cause the patient any inconvenience.

Figure 3A:
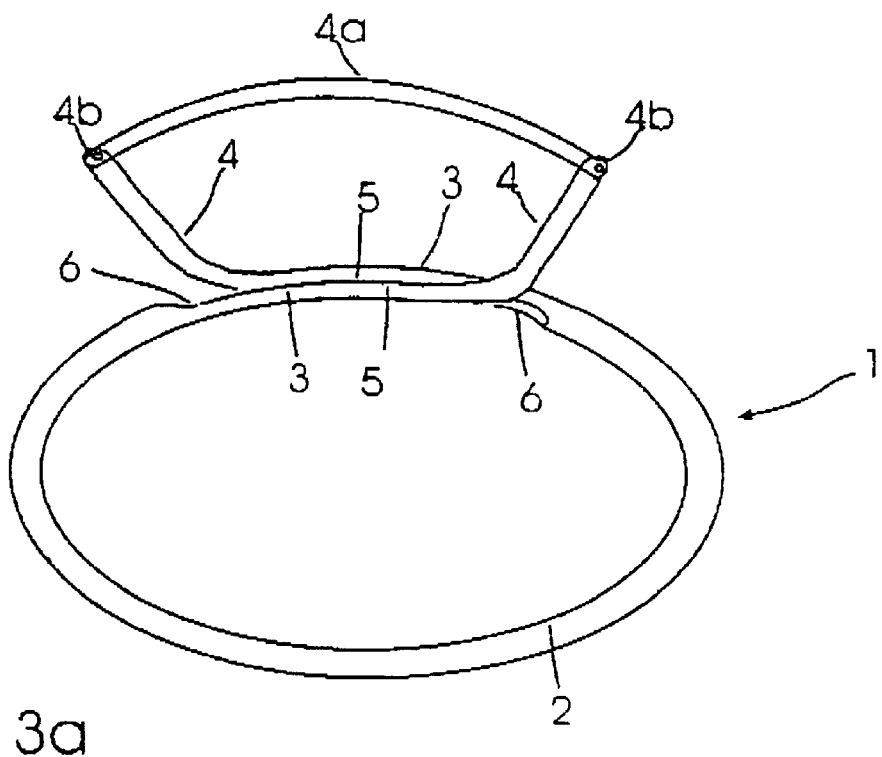
FIG. 3a is a perspective view of a modification of the embodiment in FIG. 1 when the spring ring is in rest position.
Figure 3B:
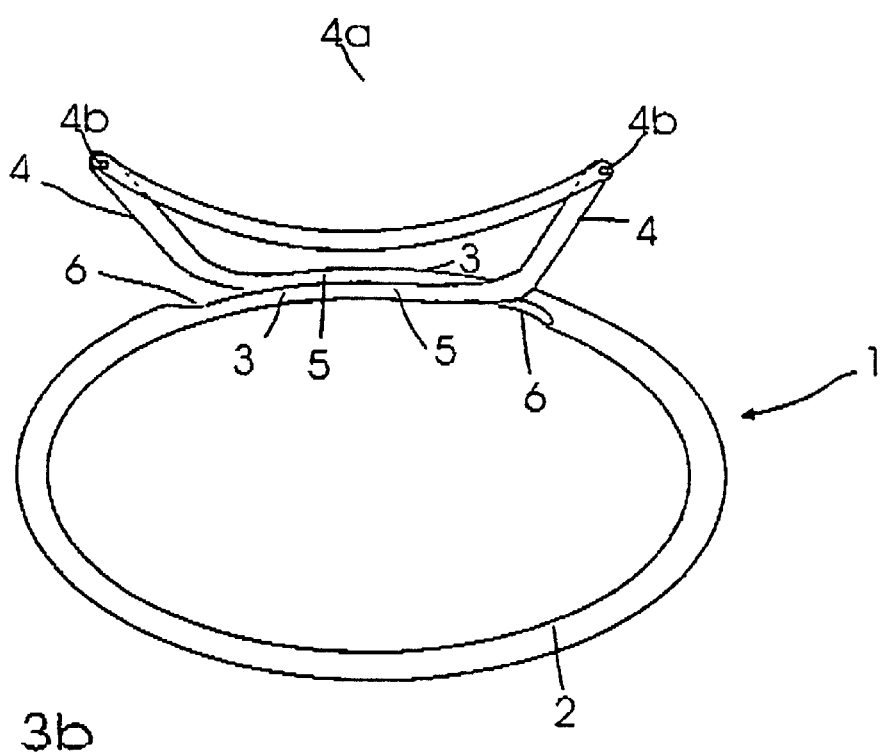
FIG. 3b is a perspective view of a modification of the embodiment in FIG. 1 when the spring ring is in a locking position.

FIGS. 3a and 3b show a modification of the embodiment in FIG. 1 in which the handles 4 are revolvably or pivotally connected to a resilient clamp 4a at their free end by means of pins 4b.

The spring ring 1 is opened by depressing the clamp 4a. The plane surfaces 6 are hereby displaced in over each other so that the spring ring 1 is opened sufficiently for it to be placed in over an implant.

When the clamp 4a is released, the spring ring 1 returns to the position in FIG. 3a, and by depressing the clamp 4a towards the spring ring 1 in the mounted state of the ostomy bag, the end parts 3 on the spring wire 2 are forced away from each other, as shown in FIG. 3b, to such an extent that the spring ring is locked.

To decouple the ostomy bag, the clamp is pulled back to the outwardly bent position shown in FIG. 3a, and the handles 4 are pressed towards each other so that the spring ring is opened and can be easily removed from the implant.

This embodiment is especially suitable for being made of plastic, and the spring ring 1 can alternatively, in an especially simple embodiment of the modification of FIGS. 3a and 3b, be designed so that the clamp 4a is designed as a part of the extension of the handles 4 so that the entire spring ring 1 forms one continuous spring wire.

It is obvious that the handles 4 can be angled in any expedient angle in relation to the end parts 3. The angling of the handles 4 in FIGS. 3a and 3b are only shown as illustrative examples.

Figure 4:
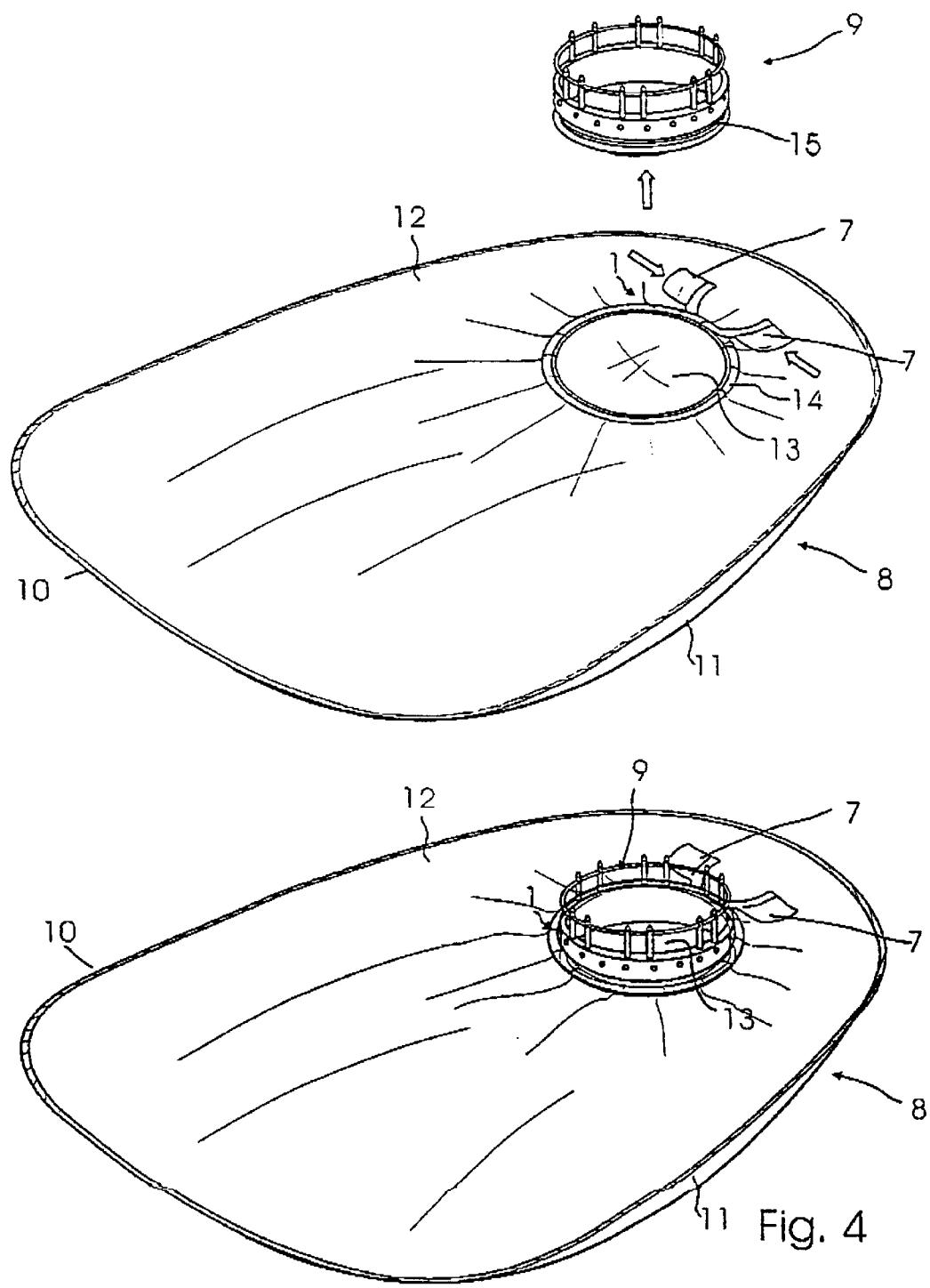
FIG. 4 is a perspective exploded view of an ostomy bag according to the invention with the spring ring in FIG. 2 and in mounted state on an implant.

FIG. 4 shows an exploded view of an ostomy bag 8 according to the invention, mounted on an implant 9. The ostomy bag 8 is designed with a wall 10, with an outer part 11 and an inner part 12 having an opening 13 and a first coupling member 14 in this case corresponding to the spring ring 1 in FIG. 2. The spring ring 1 is attached in the periphery of the opening 13 to form an edge reinforcement 14. The spring ring 1 is located inside the ostomy bag 8 between the outer part 11 and the inner part 12 and, e.g., can be glued onto the periphery of the opening 13 or can be welded together with at least an area of the inner part 12 of the flexible wall 10 around the opening 13.

When the projections 7 on the handles 4, by a pressure of e.g. thumb and index finger, are pressed in the direction of the arrow towards each other to overcome the spring power of the spring ring 1, the plane surfaces 6 of the spring ring 1 are made to slide in over each other so that the spring ring is opened for the edge reinforcement to pass over the circumferential groove 15 of the implant. When the handles 4 are released, the spring ring 1 returns to its normal position, and the first coupling member 14 of the ostomy bag is coupled in a close-fitting manner to the implant 9.

What is claimed is:

1. An ostomy bag comprising a flexible wall with an opening for receiving a stoma, and a coupling to couple the ostomy bag together with a substantially annular implant fitted around the stoma, the implant having an outer part that includes a circumferential groove therealong, the coupling comprising spring wire in ring form, and the spring ring having overlapping end parts shaped as handles and arranged to provide the spring ring, in a rest position, with a diameter that is smaller than that of the circumferential groove of the implant, wherein at least the handles of the spring ring are located inside the ostomy bag and the ostomy bag includes an opening that is provided with edge reinforcement formed by joining at least a part of the spring ring and a portion of the flexible wall of the ostomy bag, the edge reinforcement, upon coupling of the ostomy bag and the implant in a mounted state, is received in the circumferential groove of the implant, and the handles are arranged such that, when pressed towards each other, the spring ring is opened sufficiently so that the spring ring and edge reinforcement each have a diameter that is larger than that of the circumferential groove of the implant to facilitate connection of the ostomy bag to the circumferential groove of the implant or removal of the ostomy bag from the circumferential groove of the implant.

2. The ostomy bag according to claim 1, wherein the spring ring has sufficient spring power to press the edge reinforcement into abutment against the circumferential groove of the implant when the ostomy bag and the implant are in a coupled state.

3. The ostomy bag according to claim 1, wherein the edge reinforcement extends along the entire bag opening periphery.

4. The ostomy bag according to claim 1, wherein the overlapping end parts of the spring ring are provided with opposing plane surfaces which are positioned adjacent or against each other in the mounted state.

5. The ostomy bag according to claim 4, wherein the overlapping end parts, in areas of mutual contact, have diameters that combine to form a combined diameter that is essentially the same as that of the spring wire in other portions of the spring ring.

6. The ostomy bag according to claim 1, wherein the entire spring ring is located inside the ostomy bag.

7. The ostomy bag according to claim 1, wherein the handles of the spring ring are formed from ends of the spring wire of the spring ring.

8. The ostomy bag according to claim 1, wherein each handle has a resilient projection extending in opposite directions to each other.

9. The ostomy bag according to claim 1, wherein each handle includes an eye formed from ends of the spring wire of the spring ring.

10. An ostomy bag comprising a flexible wall with an opening for receiving a stoma, and a coupling to couple the ostomy bag together with a substantially annular implant fitted around the stoma, the implant having an outer part that includes a circumferential groove therealong, the coupling comprising spring wire in ring form, and the spring ring having overlapping end parts shaped as handles and arranged to provide the spring ring, in a rest position, with a diameter that is smaller than that of the circumferential groove of the implant, wherein the ostomy bag includes an opening that is provided with edge reinforcement formed by joining at least a part of the spring ring and a portion of the flexible wall of the ostomy bag, the edge reinforcement, upon coupling of the ostomy bag and the implant in a mounted state, is received in the circumferential groove of the implant, and the handles are arranged such that, when pressed towards each other, the spring ring is opened sufficiently so that the spring ring and edge reinforcement each have a diameter that is larger than that of the circumferential groove of the implant to facilitate connection of the ostomy bag to the circumferential groove of the implant or removal of the ostomy bag from the circumferential groove of the implant, and wherein the edge reinforcement is formed by at least a part of the spring ring and a portion of the flexible wall adjacent the opening of the ostomy bag, with the wall portion being wrapped at least partly around the spring wire of the spring ring.

11. An ostomy bag comprising a flexible wall with an opening for receiving a stoma, and a coupling to couple the ostomy bag together with a substantially annular implant fitted around the stoma, the implant having an outer part that includes a circumferential groove therealong, the coupling comprising spring wire in ring form, and the spring ring having overlapping end parts shaped as handles and arranged to provide the spring ring, in a rest position, with a diameter that is smaller than that of the circumferential groove of the implant, wherein the ostomy bag includes an opening that is provided with edge reinforcement formed by joining at least a part of the spring ring and a portion of the flexible wall of the ostomy bag, the edge reinforcement, upon coupling of the ostomy bag and the implant in a mounted state, is received in the circumferential groove of the implant, and the handles are arranged such that, when pressed towards each other, the spring ring is opened sufficiently so that the spring ring and edge reinforcement each have a diameter that is larger than that of the circumferential groove of the implant to facilitate connection of the ostomy bag to the circumferential groove of the implant or removal of the ostomy bag from the circumferential groove of the implant, and wherein the spring ring includes a clamp extending between the handles.

* * * * *